United States Patent
Richard et al.

(10) Patent No.: US 6,361,764 B2
(45) Date of Patent: Mar. 26, 2002

(54) INSOLUBLE S-TRIAZINE DERIVATIVES AND THEIR USE AS UV FILTERS

(75) Inventors: Hervé Richard, Villepinte; Madeleine Leduc, Paris; Alain Lagrange, Coupvray, all of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/834,910

(22) Filed: Apr. 16, 2001

Related U.S. Application Data

(63) Continuation of application No. 09/319,111, filed as application No. PCT/FR97/01995 on Nov. 6, 1997, now abandoned.

(30) Foreign Application Priority Data

Dec. 13, 1996 (FR) .............................. 96 15368

(51) Int. Cl.$^7$ .............................. A61K 7/42; A61K 7/44; A61K 7/00; A61K 31/53
(52) U.S. Cl. .......................... 424/59; 424/60; 424/400; 424/401; 514/241
(58) Field of Search ................................ 544/198, 209; 252/403

(56) References Cited

U.S. PATENT DOCUMENTS

| | | | | |
|---|---|---|---|---|
| 4,929,250 A | * | 5/1990 | Hung et al. | 544/209 |
| 5,700,394 A | * | 12/1997 | Isharani et al. | 252/302.01 |
| 5,744,127 A | * | 4/1998 | Giuseppe et al. | 544/198 |

FOREIGN PATENT DOCUMENTS

| | | |
|---|---|---|
| GB | 980886 | 1/1965 |
| JP | 03-280122 | 10/1991 |
| JP | H5-117444 | 5/1993 |
| JP | 5117444 | * 5/1993 |

* cited by examiner

*Primary Examiner*—Shelley A. Dodson
(74) *Attorney, Agent, or Firm*—Burns, Doane, Swecker & Mathis, L.L.P.

(57) ABSTRACT

The present invention relates to novel insoluble s-triazine derivatives bearing benzotriazole and/or benzothiazole groups, to a process for their preparation and to their uses in particulate form as UV screening agents, in particular in the cosmetic field.

The present invention also relates to the application of these compounds in particular to protecting the skin and the hair against ultraviolet radiation.

9 Claims, No Drawings

INSOLUBLE S-TRIAZINE DERIVATIVES AND THEIR USE AS UV FILTERS

This application is a continuation of U.S. application Ser. No. 09/319,111, filed on filed on Oct. 4, 1999, now abandoned, which was a national stage filing under 35 U.S.C. § 371 of International Application No. PCT/FR97/01995 filed on Nov. 6, 1997, which International Application was not published by the International Bureau in English on Jun. 18. 1998.

The present invention relates to novel insoluble s-triazine derivatives bearing benzotriazole and/or benzothiazole groups, to a process for their preparation and to their uses in particulate form as UV screening agents, in particular in the cosmetic field.

The present invention also relates to the use of these novel compounds for protecting the skin and/or the hair against ultraviolet radiation, or for protecting any other material which is sensitive to UV (mineral or organic glasses, plastics or the like).

It is known that light radiation with wavelengths of between 280 nm and 400 nm permit tanning of the human epidermis and that rays with wavelengths of between 280 nm and 320 nm, known as UV-B, cause skin burns and erythema which can be harmful to the development of a natural tan. For these reasons, as well as for aesthetic reasons, there is a constant demand for means for controlling this natural tanning in order thus to control the colour of the skin; this UV-B radiation should thus be screened out.

It is also known that UV-A rays, with wavelengths of between 320 nm and 400 nm, which cause tanning of the skin, are capable of inducing degradation thereof, in particular in the case of sensitive skin or of skin continually exposed to solar radiation. In particular, UV-A rays cause a loss of skin elasticity and the appearance of wrinkles, leading to premature ageing. They promote the triggering of the erythemal reaction or amplify this reaction in certain individuals and can even be the cause of phototoxic or photoallergic reactions. Thus, for aesthetic and cosmetic reasons such as the conservation of the skin's natural elasticity, for example, more and more people wish to control the effect of UV-A rays on their skin. It is thus desirable also to screen out UV-A radiation.

A large number of compounds have already been proposed as sunscreens, essentially in the form of soluble organic screening agents or of insoluble inorganic compounds. These screening agents must be able to absorb or block out the harmful rays of the sun while remaining harmless for the user.

In this respect, and in order to limit any risks of allergy on the skin caused by the organic screening agents on account of their solubility, inorganic pigments such as zinc oxide or titanium oxide are increasingly used to screen out UV rays. However, these inorganic pigments have the drawback of being sensitive to solar radiation (phenomenon known as photo-bluing). Moreover, for equivalent amounts, these inorganic pigments are less effective in protecting against UV than the abovementioned organic screening agents.

After considerable-research conducted in the field of photoprotection mentioned above, the Applicant has now discovered novel non-mineral insoluble UV screening agents which are capable of absorbing both in the UV-A range and in the UV-B-range, and which have the advantage of cumulating both the property of diffusion, since they are solid organic pigments, and the property of absorption.

This discovery forms the basis of the invention.

Thus, according to the present invention, novel compounds are now proposed corresponding to formula (I) below:

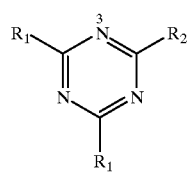

(I)

in which the symbols $R_1$, which may be identical or different, are radicals of formula (II) or (III) below:

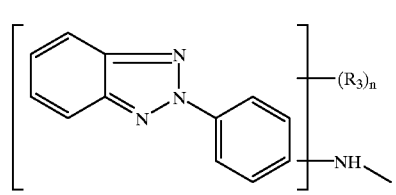

(II)

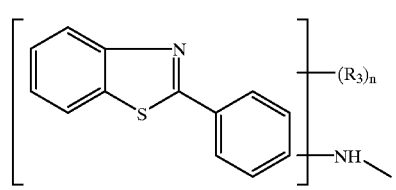

(III)

$R_2$ is a halogen, $N(R_4)_2$, $OR_5$ or a group $R_1$, $R_3$, which may be identical or different, are linear or branched $C_1$–$C_8$ alkyl radicals, $C_1$–$C_3$ alkoxy radicals, it being understood that, in the latter case, two adjacent groups $R_3$ on the same aromatic ring can together form an alkylidenedioxy group in which the alkylidene group contains 1 or 2 carbon atoms, OH, $NHCOCH_3$ or $NH_2$, $R_4$, which may be identical or different, denote a hydrogen atom or a linear or branched $C_1$–$C_6$ alkyl. radical, it being possible for two groups $R_4$ together to form a ring of 4 or 5 carbon atoms, n is 0, 1, 2, 3 or 4, $R_5$ is a hydrogen or a $C_1$–$C_6$ alkyl radical.

In a preferred embodiment of the invention, the radicals $R_1$, which may be identical or different, denote the radicals of formula (II') or (III') below:

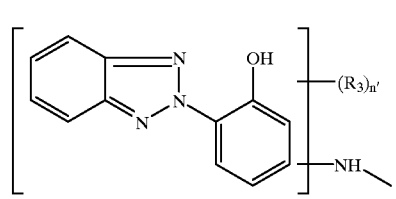

(II')

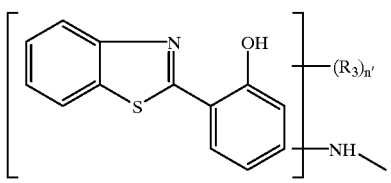

in which the radicals $R_3$ have the same meaning as those of formulae (II) and (III) and n' is 0, 1, 2 or 3.

In one preferred embodiment of the invention, the two radicals $R_1$ and the radical $R_2$ are identical. Also preferably, the two radicals $R_1$ and the radical $R_2$ are identical and denote a radical of formula (II').

These novel insoluble s-triazine compounds can be used as sunscreens for human skin and the hair, and also as agents for protecting against light in the plastics industry.

The derivatives of the invention are insoluble compounds capable of simultaneously absorbing in the UV-A range and in the UV-B range. The radicals of formulae (II) and (III) are screening units which generally absorb UV-A radiation; the novel insoluble compounds in accordance with the present invention, substituted with these radicals, have the unexpected and surprising advantage of absorbing both in the UV-A range and in the UV-B range.

Moreover, besides their screening and dispersing properties, these novel derivatives have good chemical and photochemical stability. On account of their insolubility, they present little risk of penetration into the epidermis. These compounds are thus all indicated for the preparation of compositions intended for the antisun protection of the skin and the hair.

For the purposes of the present invention, the expression insoluble or substantially insoluble compounds means compounds whose solubility in water is less than 0.1% by weight, whose solubility in liquid petroleum jelly is less than 1% by weight and, lastly, whose solubility in a mixture of triglyceride esters such as "Miglyol 812" sold by the company Dynamit Nobel is less than 2%, also by weight.

A subject of the present invention is also a process for preparing the compounds of formula (I) defined above, which consists in reacting a compound of formula (IV) below with the derivatives of formulae $R_1H$ and $R_2H$ according to the reaction scheme below:

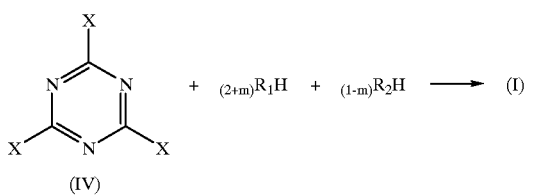

in which:
$R_1$ and $R_2$ correspond to the definitions given for formula (I) above,
X represents a halogen, in particular chlorine or bromine,
m is 0 or 1.

The compounds $R_1H$ can be prepared according to known methods as described in patents DE 2,128,005, EP 221,630, FR 1,324,897 or in the article by T. Konstantinova et al., Polymer Degradation and Stability, 43, 187 (1994).

Thus, as aminobenzotriazole derivatives, mention may be made of:

2-(2-hydroxy-5-aminophenyl)-5-methoxybenzotriazole described in document EP 221,630, 2-(2-hydroxy-4-aminophenyl)benzotriazole, 2-(2-hydroxyphenyl)-5-aminobenzotriazole and 2-(2-hydroxy-5-methylphenyl)-5-aminobenzotriazole described in documents U.S. Pat. No. 3,159,646 and GB 1,346,764, 2-(2-hydroxy-5-aminophenyl)benzotriazole described in the document J. Belusa et al., Chem. Zvesti, 2-(2-hydroxy-5-aminophenyl)-5-chlorobenzotriazole and 2-(2-hydroxy-4-aminophenyl)-5-chlorobenzotriazole described in the document H. S. Freeman et al., Dyes and Pigments, 20, 171 (1992)), 2-(2-hydroxy-3-amino-5-methylphenyl)benzotriazole, 2-(2-hydroxy-3-amino-5-tert-butylphenyl) benzotriazole and 2-(2-hydroxy-3-amino-5-tert-octylphenyl)benzotriazole, which can be prepared according to methods described in documents DE 2,128,005 and GB 1,346,764.

As aminobenzothiazole derivative, mention may be made, for example, of 2-(para-aminophenyl)-6-methylbenzothiazole described in document U.S. Pat. No. 2,334,348.

The above reactions can optionally be carried out in the presence of a solvent (toluene, xylene or acetone/water).

Among the compounds in accordance with the invention, mention may be made more particularly of:

2,4,6-tris[(3'-benzotriazol-2-yl-2'-hydroxy-5'-methyl) phenylamino]-s-triazine, 2,4,6-tris[(3'-benzotriazol-2-yl-2'-hydroxy-5'-tert-octyl) phenylamino]-s-triazine.

These novel insoluble or substantially insoluble s-triazine derivatives can be brought into a suitable particulate form by any ad-hoc means such as, in particular, dry-grinding or grinding in a solvent medium, screening, atomization, micronization or spraying. They can then be used as pigments for the antisun protection of human skin and the hair. They can also be used as agents for protecting against light in the plastics industry, in the glass industry (packaging, optical glasses, in particular for spectacles) and the like.

A subject of the present invention is also a composition intended for protecting a material which is sensitive to ultraviolet radiation, in particular to solar radiation, comprising an effective amount of at least one compound of formula (I).

More particularly, when the sensitive material to be protected is the skin and/or the hair, this composition is in the form of a cosmetic composition comprising, in a cosmetically acceptable support, an effective amount of at least one compound of formula (I).

Preferably, the compounds according to the invention are used, in the cosmetic-compositions in accordance with the invention, in particulate form, the average size of the particles being less than 20 µm.

The compound(s) of formula (I) can be present in the cosmetic composition according to the invention in proportions of between 0.1 and 20% by weight, relative to the total weight of the composition, preferably between 0.1 and 15%.

The cosmetic composition of the invention can be used as a composition for protecting the human epidermis or the hair or as an antisun composition.

Needless to say, the compositions according to the invention can contain one or more additional hydrophilic or lipophilic sunscreens which are active in the UVA and/or UVB range (absorbers), other than those of the present invention. These additional screening agents can be chosen in particular from cinnamic derivatives, salicylic derivatives, camphor derivatives, triazine derivatives other than the compounds in accordance with the present invention, benzophenone derivatives, dibenzoylmethane derivatives, Z,Z-diphenylacrylate derivatives, p-aminobenzoic acid derivatives, and the screening polymers and screening silicones described in patent application WO-93/04665. Other examples of organic screening agents are given in patent application EP-A-0,487,404.

The compositions according to the invention can also contain agents for artificially tanning and/or browning the skin (self-tanning agents), such as, for example, dihydroxyacetone (DHA).

The compositions according to the invention can also contain pigments or alternatively nanopigments (average size of the primary particles: generally between 5 nm and 100 nm, preferably between 10 nm and 50 nm), of coated or uncoated metal oxides, such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Conventional coating agents are, moreover, alumina and/or aluminium stearate. Such coated or uncoated metal oxide nanopigments are described in particular in patent applications EP-A-0,518,772 and EP-A-0,518,773.

The compositions according to the invention can also comprise conventional cosmetic adjuvants chosen in particular from fatty substances, organic solvents, ionic or nonionic thickeners, softeners, antioxidants, opacifiers, stabilizers, emollients, silicones, α-hydroxy acids, antifoaming agents, moisturizers, vitamins, fragrances, preserving agents, surfactants, fillers, sequestering agents, polymers, propellants, basifying or acidifying agents, dyes or any other ingredient usually used in cosmetics, in particular for manufacturing antisun compositions in is emulsion form.

The fatty substances can consist of an oil or a wax or mixtures thereof, and they also comprise fatty acids, fatty alcohols and fatty acid esters. The oils can be chosen from animal, plant, mineral or synthetic oils and in particular from liquid petroleum jelly, liquid paraffin, volatile or non-volatile silicone oils, isoparaffins, poly-α-olefins, fluoro oils and perfluoro oils. Similarly, the waxes can be chosen from animal, fossil, plant, mineral or synthetic waxes which are known per se.

Among the organic solvents, mention may be made of lower alcohols and polyols.

The thickeners can be chosen in particular from crosslinked polyacrylic acids and modified or unmodified guar and cellulose gums such as. hydroxypropyl guar gum, methylhydroxyethylcellulose, hydroxypropylmethylcellulose or hydroxyethylcellulose.

Needless to say, a person skilled in the art will take care to select the optional additional compound(s) mentioned above and/or the amounts thereof such that the advantageous properties intrinsically associated with the compound in accordance with the invention are not, or are not substantially, adversely affected by the addition(s) envisaged.

When the composition according to the invention is used for protecting the human epidermis against UV rays, or as an antisun composition, it can be in the form of a suspension or a dispersion in solvents or fatty substances, in the form of a nonionic vesicle dispersion or alternatively in the form of an emulsion, preferably of oil-in-water type, such as a cream or a milk, in the form of an ointment, a gel, a cream-gel, a solid tube, a stick, an aerosol mousse or a spray.

When the composition according to the invention is used for protecting the hair, it can be in the form of a shampoo, a lotion, a gel, an emulsion, a nonionic vesicle dispersion or a lacquer for the hair and can constitute, for example, a rinse-out composition, to be applied before or after shampooing, before or after dyeing or bleaching, before, during or after permanent-waving or straightening the hair, a styling or treating lotion or gel, a blow-drying or hairsetting lotion or gel, or a composition for permanent-waving, straightening, dyeing or bleaching the hair.

The compositions of the invention can be prepared according to the techniques which are well known to those skilled in the art, in particular those intended for the preparation of emulsions of oil-in-water or water-in-oil type.

When the sensitive material to be protected is an organic and/or mineral glass or a plastic, the compositions according to the invention can be in the form of a varnish which is applied to the said sensitive material in order to protect it against ultraviolet radiation.

A subject of the present invention is also the use of at least one compound of formula (I) in, or for the manufacture of, compositions intended for protecting materials which are sensitive to ultraviolet radiation, in particular to solar radiation.

In particular, a subject of the invention is the use of at least one compound of formula (I) in, or for the manufacture of, cosmetic compositions for protecting the skin and/or the hair against ultraviolet radiation, in particular solar radiation.

A subject of the present invention is also the use of at least one compound of formula (I) in, or for the manufacture of, varnishes intended to protect organic and/or mineral glasses or plastics against ultraviolet radiation, in particular solar radiation.

The compounds of the invention can also be incorporated directly into plastics, or into other materials which are sensitive to ultraviolet radiation, in order to protect these materials against the said radiation.

A subject of the present invention is thus also a process for protecting a material which is sensitive to ultraviolet and/or solar radiation against the said radiation, this process consisting in applying to, or incorporating into, the said sensitive material an effective amount of a compound of formula (I) or of a composition containing at least one compound of formula (I).

In particular, the process according to the invention can consist in applying an effective amount of a cosmetic composition as defined above to the skin and/or the hair.

In another embodiment of the invention, the process according to the invention consists in incorporating into a plastic an effective amount of a compound of formula (I) or of a composition containing at least one compound of formula (I) in order to protect the said plastic against ultraviolet radiation, in particular against solar radiation.

Thus, one subject of the invention is a plastic composition protected by such a process.

In another embodiment of the invention, the process according to the invention consists in applying an effective amount of the said compound or of the said composition to the surface of a mineral or organic glass.

Thus, lastly, a final subject of the invention is a glassware composition protected by this process.

Concrete, but in no way limiting, examples illustrating the invention will now be given.

EXAMPLE 1

Preparation of 2,4,6-tris[(3'-benzotriazol-2-yl-2'-hydroxy-5'-methyl)phenylamino]-s-triazine

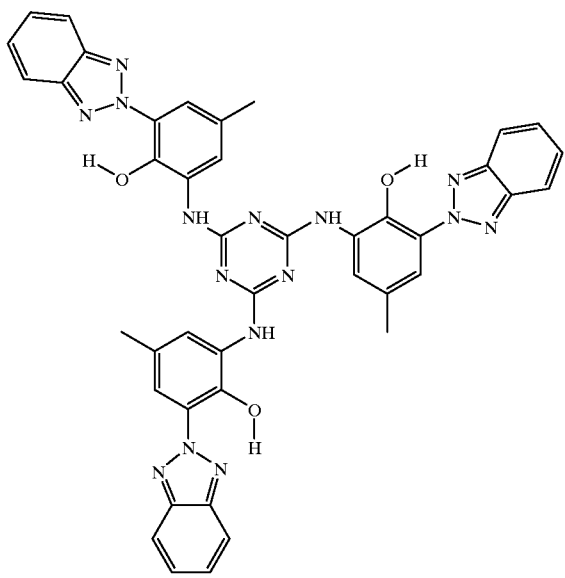

A mixture of 2-(2-hydroxy-3-amino-5-methylphenyl)benzotriazole.(1.2 g, 5×10$^{-3}$ mol) and cyanuric chloride (0.276 g, 1.5×10$^{-3}$ mol) in 50 ml of xylene is refluxed for 12 hours under nitrogen. A precipitate forms, which is filtered off, rinsed with xylene and dried under vacuum. The derivative is thus obtained (1 g, yield=83%), with the following characteristics:

pale yellow powder m.p. >270° C. Elemental analysis for $C_{42}H_{33}N_{15}O_3$:

| theory | C: 63.39 | H: 4.18 | N: 26.40 |
|---|---|---|---|
| found | C: 64.09 | H: 4.25 | N: 26.12 |

This 2,4,6-tris[(3'-benzotriazol-2-yl-2'-hydroxy-5'-methyl)phenylamino]-s-triazine was screened at 50 μm through a screen of stainless steel-gauze stainless steel assembly. Next, it was dispersed in white petroleum jelly sold under the trade name "Codex 236" by the company Sarega at the melting point of the petroleum jelly and in a proportion of 5 g of screened 2,4,6-tris[(3'-benzotriazol-2-yl-2'-hydroxy-5'-methyl) phenylamino]-s-triazine per 100 g of petroleum jelly. This mixture was then treated with ultrasound in order to ensure homogeneous dispersion. A film 10 Am thick was analysed.

The solid UV absorption spectrum was obtained using a Shimadzu UV 2101 PC spectrophotometer and is is represented in FIG. 1.

It is clearly seen in this figure that the, 2,4,6-tris[(3'-benzotriazol-2-yl-2'-hydroxy-5'-methyl)-phenylamino]-s-triazine absorbs throughout the UV radiation range (280–400 nm).

EXAMPLE 2

Preparation of 2,4,6-tris[(3'-benzotriazol-2-yl-2'-hydroxy-5'-tert-octyl)phenylaminol]-s-triazine

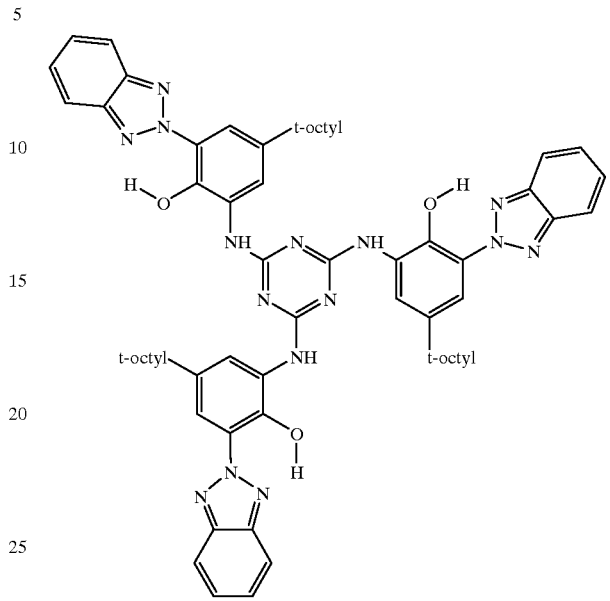

2-(2-hydroxy-3-amino-5-tert-octylphenyl)benzotriazole (3.38 g, 0.01 mol) in 50 ml of xylene is introduced into a fully equipped round-bottomed flask. Cyanuric chloride (0.553 g, 3×10$^{-3}$ mol) is introduced portionwise over 30 minutes at room temperature, under a stream of nitrogen, and the mixture is heated to 60° C. The mixture is left at this temperature for 1 hour and is then refluxed for 3 hours 30 minutes. The clear mixture is cooled to about 60° C.; 60 ml of ethanol are added thereto and the precipitate obtained is filtered off and washed with ethanol and then with water. The derivative (3.3 g, 100% yield) is thus obtained, with the following characteristics:

pale yellow powder m.p. >270° C.;

UV (CHCl$_3$)$\lambda_{max}$=326 nm, $\epsilon_{max}$=68,600;

UV: (in solid form): see FIG. 2 (absorption spectrum);

Elemental analysis for $C_{63}H_{75}N_{15}O_3$:

| theory | C: 69.40 | H: 6.93 | N: 19.27 |
|---|---|---|---|
| found | C: 69.39 | H: 6.96 | N: 18.95 |

The solid UV absorption spectrum of this 2,4,6-tris[(3'-benzotriazol-2-yl-2'-hydroxy-5'-tert-octyl)phenylamino]-s-triazine was measured according to the same procedure as in Example 1. This spectrum is represented in FIG. 2. It is also clearly seen in this FIG. 2 that the 2,4,6-tris[(3'-benzotriazol-2-yl-2'-hydroxy-5'-tert-octyl)phenylamino]-s-triazine absorbs throughout the UV radiation range (280–400 nm).

EXAMPLE 3

A concrete example of a cosmetic composition in the form of an oil-in-water emulsion is given below (the amounts are expressed as a % by weight relative to the total weight of the composition):

| | |
|---|---|
| mixture of cetylstearyl alcohol and of cetylstearyl alcohol oxyethylenated with 33 mol of ethylene oxide, sold under the trade name "Sinnovax AO" by Henkel | 7% |
| non-self-emulsifying mixture of glyceryl mono- and distearate | 2% |
| cetyl alcohol | 1.5% |
| silicone oil | 1.5% |
| diisopropyl adipate | 15% |
| derivative of Example 1 | 5% |
| glycerol | 20% |
| fragrance, preserving agents | qs |
| water | qsp 100% |

This composition was prepared in the following way: after preparing the emulsion, the screening agent was dispersed at about 40° C. The cream obtained was then homogenized with a triple-roller machine.

This composition absorbs throughout the UV radiation range.

What is claimed is:

1. A cosmetic composition intended for protecting the skin and/or the hair against ultraviolet and/or solar radiation, comprising an effective amount of one or more compounds of formula (I) below, in the form of particles:

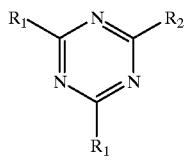
(I)

in which the symbols $R_1$, which may be identical or different, are radicals of formula (II) or (III) below:

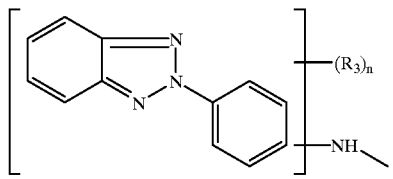
(II)

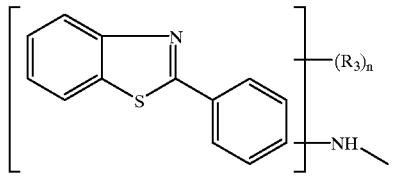
(III)

wherein:
$R_2$ is a halogen, $N(R_4)_2$, $OR_5$ or a group $R_1$,
$R_3$, which may be identical or different, are linear or branched $C_1$–$C_8$ alkyl radicals, $C_1$–$C_3$ alkoxy radicals, OH, $NHCOCH_3$ or $NH_2$, with the proviso that two adjacent $R_3$ groups on the same aromatic ring can together form an alkylidenedioxy group having 1 or 2 carbon atoms, $R_4$, which may be identical or different, denote a hydrogen atom or a linear or branched $C_1$–$C_6$ alkyl radical, with the proviso that two $R_4$ groups together with the nitrogen may form a ring having 4 or 5 carbon atoms, n is 0, 1, 2, 3 or 4, and R5 is a hydrogen or a $C_1$–$C_6$ alkyl radical.

2. A composition according to claim 1, wherein the average size of the said particles is less than 20 μm.

3. A composition according to claim 1, which contains from 0.1 to 15% by weight, relative to the total weight of the composition, of said compound of formula (I).

4. A method for protecting the skin and/or the hair against ultraviolet and/or solar radiation, comprising applying or incorporating one or more cosmetic compositions according to claim 1.

5. Process for protecting the skin and/or the hair against ultraviolet and/or solar radiation, comprising applying an effective amount of one or more cosmetic compositions as defined in claim 1 to the skin and/or the hair.

6. A composition according to claim 1, wherein the radicals $R_1$, which may be identical or different, denote the radicals of formula (II') or (III') below:

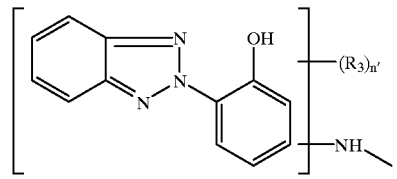
(II')

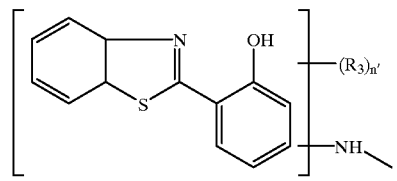
(III')

in which the radicals $R_3$ are as defined in formulae (II) and (III) of claim 1 and n' is 0, 1, 2 or 3.

7. A composition according to claim 1, wherein the radicals $R_1$ and $R_2$ are identical.

8. A composition according to claim 7, wherein said radicals $R_1$ and $R_2$ denote a radical of formula (II').

9. A composition according to claim 8, wherein the compound of formula (I) is 2,4,6-tris[(3'-benzotriazol-2-yl-2'-hydroxy-5'-methyl)phenylamino]-s-triazine or 2,4,6-tris[(3'-benzotriazol-2-yl-2'-hydroxy-5'-tert-octyl)phenylamino]-s-triazine.

* * * * *